(12) United States Patent
Arazi et al.

(10) Patent No.: US 9,798,857 B2
(45) Date of Patent: Oct. 24, 2017

(54) METHOD AND APPARATUS FOR PROVIDING AN INTEGRATED DISPLAY OF CLINICAL DATA

(71) Applicant: Change Healthcare LLC, Alpharetta, GA (US)

(72) Inventors: Ohad Arazi, Vancouver (CA); Joe Biegel, Vancouver (CA)

(73) Assignee: Change Healthcare LLC, Alpharetta, GA (US)

(*) Notice: Subject to any disclaimer, the term of this patent is extended or adjusted under 35 U.S.C. 154(b) by 264 days.

(21) Appl. No.: 13/827,315

(22) Filed: Mar. 14, 2013

(65) Prior Publication Data

US 2014/0143719 A1     May 22, 2014

Related U.S. Application Data

(60) Provisional application No. 61/729,079, filed on Nov. 21, 2012.

(51) Int. Cl.
    *G06F 3/048*     (2013.01)
    *G06F 19/00*     (2011.01)

(52) U.S. Cl.
    CPC .......... *G06F 19/322* (2013.01); *G06F 19/324* (2013.01)

(58) Field of Classification Search
    USPC ....................................................... 715/810
    See application file for complete search history.

(56) References Cited

U.S. PATENT DOCUMENTS

| | | | | |
|---|---|---|---|---|
| 2007/0063998 A1* | 3/2007 | Mahesh | ................ | G06F 19/321 345/419 |
| 2009/0228299 A1* | 9/2009 | Kangarloo | ............ | G06F 19/321 705/2 |
| 2009/0248447 A1* | 10/2009 | Niwa | .................. | G06F 19/3487 705/3 |
| 2010/0169355 A1* | 7/2010 | Rosenberger | .......... | G06Q 10/10 707/766 |

* cited by examiner

*Primary Examiner* — William Trapanese
(74) *Attorney, Agent, or Firm* — Alston & Bird LLP (57) ABSTRACT

A method, apparatus and computer program product therefore provide an integrated display of clinical data. In this regard, the method, apparatus and computer program product may provide access to patient clinical data during a medical study. The relevant clinical data may be obtained from patient medical records, and displayed along with information from the medical study. An interface may be provided, allowing for selection of one or more portions of the relevant clinical data by a user. The portion of relevant clinical data associated with the particular interface element may be displayed. The method, apparatus, and computer program product may also incorporate adaptive learning techniques, monitoring user input during various study operations to identify particular relevant clinical data and/or interface elements that are selected by the user during the study.

18 Claims, 6 Drawing Sheets

METHOD AND APPARATUS FOR PROVIDING AN INTEGRATED DISPLAY OF CLINICAL DATA

CROSS REFERENCE TO RELATED APPLICATIONS

This application claims priority to U.S. Provisional Application No. 61/729,079, filed Nov. 21, 2012, the entire contents of which are incorporated herein by reference.

TECHNOLOGICAL FIELD

An example embodiment of the present invention relates generally to providing access to medical records, and, more particularly, to displaying clinical data in conjunction with medical imaging data.

BACKGROUND

The use of electronic medical records offers many advantages to both patients and practitioners. Files may be maintained on a network, allowing easy access to patient histories, studies, analyses, and other records. These files may be maintained in a digital format that is easy to transmit or share among medical professionals, reducing the need for redundant or repeat studies and diagnoses. Patients that wish to obtain a second opinion or change doctors no longer need to arrange for the transportation of physical files, and medical providers may see dramatic benefits in administrative overhead tasks such as faxing, photocopying, or mailing documents.

However, these electronic medical records are often provided in a raw "data dump" format. Although some filing systems provide the ability to tag or annotate documents, a practitioner may still be confronted with dozens or hundreds of individual documents, of which only a few may be relevant to a particular task. While an internist or family doctor may have a need to be familiar with the patient's entire medical history, patients often receive referrals to specialists for particular systems or diagnoses. The referral to the specialist or prescription for a study may only include a very brief description of the patient and the symptoms (e.g., age, gender, type of study ordered, general indications), without providing insight to possibly relevant elements of the patient's medical records.

Although the patient's medical records may include additional data that is relevant to the specialist, the sheer amount of available data may result in a low "signal to noise" ratio of relevant data to irrelevant data. It is rarely an efficient use of the specialist's time to comb through the patient's entire medical history to identify such pertinent information. In the particular case of medical imaging, radiologists are trained to analyze data in a visual manner using specialized equipment, and it is impractical and inefficient to step away from an imaging device to access the text-based records via a separate application.

BRIEF SUMMARY

A method, apparatus and computer program product are therefore provided according to an example embodiment of the present invention in order to provide an integrated display of clinical data. In this regard, the method, apparatus and computer program product of an example embodiment may provide access to patient clinical data during a medical study, such as a medical imaging operation. Relevant patient clinical data may be determined based on the type of study performed. The relevant clinical data may be extracted or otherwise obtained from patient medical records, and displayed along with information from the medical study. An interface may be provided, allowing for selection of one or more portions of the relevant clinical data by a user. Upon selection of a particular interface element, the portion of relevant clinical data associated with the particular interface element may be displayed. Embodiments may also incorporate adaptive learning techniques, monitoring user input during various study operations to identify particular relevant clinical data and/or interface elements that are selected by the user during the study. Interface elements and/or relevant clinical data that are selected may be used to populate a set of user preferences, so that the selected interface elements and/or clinical data are presented as options during future studies or imaging operations of the same type.

Embodiments may provide for a method for providing an integrated display of clinical data. The method may include receiving medical study data associated with a patient and determining, using a processor, one or more sets of clinical data based on the medical study data. The one or more sets of clinical data may be associated with the patient. The method may also include generating an interface comprising a plurality of interface elements. The interface may provide access to the one or more sets of clinical data via selection of one at least one of the plurality of interface elements.

Embodiments may also provide an apparatus. The apparatus may include processing circuitry. The processing circuitry may be configured to receive medical study data associated with a patient and to determine one or more sets of clinical data based on the medical study data. The one or more sets of clinical data may be associated with the patient. The processing circuitry may be further configured to generate an interface comprising a plurality of interface elements. The interface may provide access to the one or more sets of clinical data via selection of one at least one of the plurality of interface elements.

Embodiments may also provide a computer program product including at least one computer-readable storage medium bearing computer program instructions embodied therein for use with a computer. The computer program instructions may include program instructions configured to receive medical study data associated with a patient and to determine one or more sets of clinical data based on the medical study data. The one or more sets of clinical data may be associated with the patient. The computer program instructions may further include program instructions to generate an interface comprising a plurality of interface elements. The interface may provide access to the one or more sets of clinical data via selection of one at least one of the plurality of interface elements.

BRIEF DESCRIPTION OF THE DRAWINGS

Having thus described certain embodiments of the invention in general terms, reference will now be made to the accompanying drawings, which are not necessarily drawn to scale, and wherein:

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

A method, apparatus and computer program product are provided in accordance with an example embodiment of the present invention in order to provide an integrated display of clinical data. In this regard, a method, apparatus and computer program product of an example embodiment may receive information from a medical study, such as a medical image. Based on the medical study, clinical data relevant to the study may be identified. The relevant clinical data may be used to select a set of interface elements, allowing a user to select an interface element to view clinical data for the patient associated with the interface element. In this manner, the integrated display may provide for efficient viewing of patient electronic medical record data while a medical practitioner performs a medical study or reviews data from a medical study.

Figure 1:
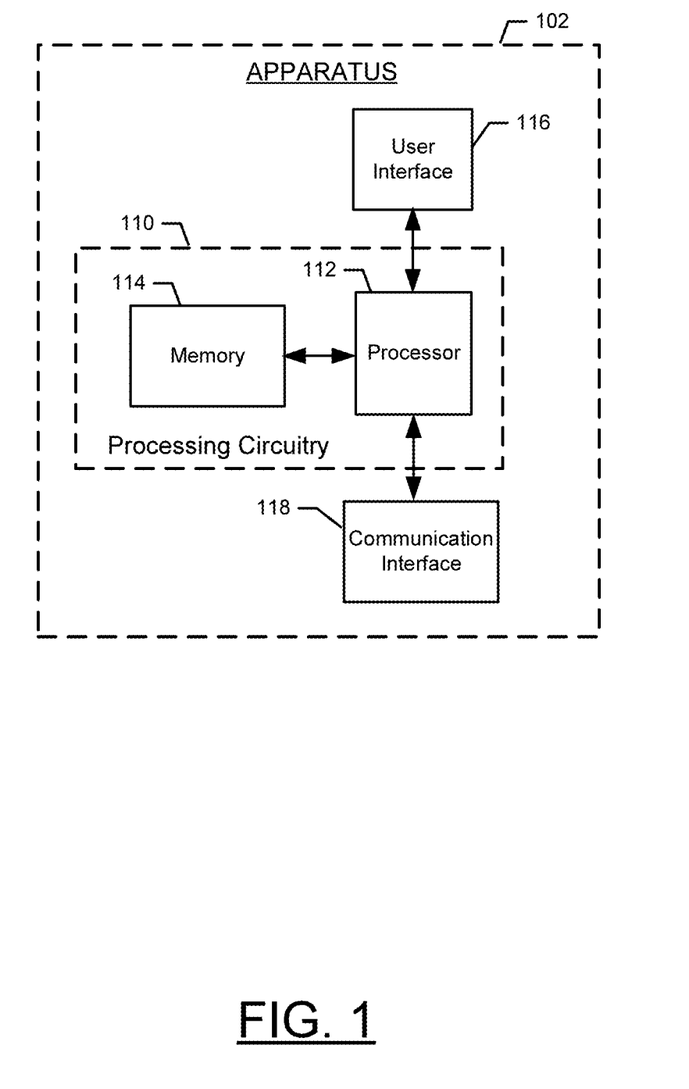
FIG. 1 is a block diagram of an apparatus that may be specifically configured in accordance with example embodiments of the present invention.

FIG. 1 illustrates a block diagram of an apparatus 102 in accordance with some example embodiments. The apparatus 102 may be any computing device configured to display data from a medical study. The apparatus 102 may further provide an interface allowing a practitioner to select patient clinical data that may be relevant to the study. The patient clinical data may be determined to be relevant based on correlations between the context of the patient clinical data and the study data. For example, the provided patient clinical data may be relevant to the particular procedure type of the study, the modality of the study, the patient's orientation during the study, the region of the patient's body examined in the study, or the personal preferences of the practitioner examining the study. Embodiments of the apparatus may further incorporate learning techniques to identify relevant clinical data for various types of studies, and provide interface elements for selecting the relevant clinical data based on the identified relevant clinical data associated with a particular study being viewed by the practitioner. The apparatus 102 may interface with one or more patient electronic medical record systems to obtain clinical data relevant to the patient. The apparatus 102 may further associate a patient for which the medical study is performed with a set of patient electronic medical records to retrieve the clinical data. For example, in some particular embodiments, the apparatus 102 may be configured to perform or otherwise assist with medical diagnostic and/or imaging operations. As a specific example, the apparatus 102 may include a plurality of displays, with a set of imaging data for a particular patient displayed on a first screen, and an interface for viewing patient clinical data on a second display. The interface for viewing patient clinical data may be populated with interface elements associated with the particular imaging operation or type of image being viewed on the first display.

It should be noted that the components, devices or elements illustrated in and described with respect to FIG. 1 below may not be mandatory and thus some may be omitted in certain embodiments. Additionally, some embodiments may include further or different components, devices or elements beyond those illustrated in and described with respect to FIG. 1.

The apparatus 102 may include or otherwise be in communication with processing circuitry 110 that is configurable to perform actions in accordance with one or more example embodiments disclosed herein. In this regard, the processing circuitry 110 may be configured to perform and/or control performance of one or more functionalities of the apparatus 102 (e.g., functionalities of a computing device on which the apparatus 102 may be implemented) in accordance with various example embodiments, and thus may provide means for performing functionalities of the apparatus 102 (e.g., functionalities of a computing device on which the apparatus 102 may be implemented) in accordance with various example embodiments. The processing circuitry 110 may be configured to perform data processing, application execution and/or other processing and management services according to one or more example embodiments. In some embodiments, the apparatus 102 or a portion(s) or component(s) thereof, such as the processing circuitry 110, may be embodied as or comprise a chip or chip set. In other words, the apparatus 102 or the processing circuitry 110 may comprise one or more physical packages (e.g., chips) including materials, components and/or wires on a structural assembly (e.g., a baseboard). The apparatus 102 or the processing circuitry 110 may therefore, in some cases, be configured to implement an embodiment of the invention on a single chip or as a single "system on a chip." As such, in some cases, a chip or chipset may constitute means for performing one or more operations for providing the functionalities described herein.

In some example embodiments, the processing circuitry 110 may include a processor 112 and, in some embodiments, such as that illustrated in FIG. 1, may further include memory 114. The processing circuitry 110 may be in communication with or otherwise control a user interface 116 and/or a communication interface 118. As such, the processing circuitry 110 may be embodied as a circuit chip (e.g., an integrated circuit chip) configured (e.g., with hardware, software or a combination of hardware and software) to perform operations described herein.

The processor 112 may be embodied in a number of different ways. For example, the processor 112 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor 112 may comprise a plurality of processors. The plurality of processors may be in operative communication with each other and may be collectively configured to perform one or more functionalities of the apparatus 102 as described herein. The plurality of processors may be embodied on a single computing device or distributed across a plurality of computing devices collectively configured to function as the apparatus 102. In some example embodiments, the processor 112 may be configured to execute instructions stored in the memory 114 or otherwise accessible to the processor 112. As such, whether configured by hardware or by a combination of hardware and software, the processor 112 may represent an entity (e.g., physically embodied in circuitry—in the form of processing circuitry 110) capable of performing operations according to embodiments of the present invention while configured accordingly. Thus, for example, when the processor 112 is embodied as an ASIC, FPGA or the like, the processor 112 may be specifically configured hardware for conducting the operations described herein. Alternatively, as another example, when the processor 112 is embodied as an executor of software instructions, the instructions may specifically configure the processor 112 to perform one or more operations described herein.

In some example embodiments, the memory 114 may include one or more non-transitory memory devices such as, for example, volatile and/or non-volatile memory that may be either fixed or removable. In this regard, the memory 114 may comprise a non-transitory computer-readable storage medium. It will be appreciated that while the memory 114 is illustrated as a single memory, the memory 114 may comprise a plurality of memories. The plurality of memories may be embodied on a single computing device or may be distributed across a plurality of computing devices collectively configured to function as the apparatus 102. The memory 114 may be configured to store information, data, applications, instructions and/or the like for enabling the apparatus 102 to carry out various functions in accordance with one or more example embodiments. For example, the memory 114 may be configured to buffer input data for processing by the processor 112. Additionally or alternatively, the memory 114 may be configured to store instructions for execution by the processor 112. As yet another alternative, the memory 114 may include one or more databases that may store a variety of files, contents or data sets. Among the contents of the memory 114, applications may be stored for execution by the processor 112 in order to carry out the functionality associated with each respective application. In some cases, the memory 114 may be in communication with one or more of the processor 112, user interface 116, or communication interface 118 via a bus or buses for passing information among components of the apparatus 102.

The user interface 116 may be in communication with the processing circuitry 110 to receive an indication of a user input at the user interface 116 and/or to provide an audible, visual, mechanical or other output to the user. As such, the user interface 116 may include, for example, a keyboard, a mouse, a joystick, one or more displays, a touch screen display, a microphone, a speaker, a Light Emitting Diode (LED), a lighting device, an electronic sensor for capturing human body movements, and/or other input/output mechanisms. In embodiments in which the apparatus 102 is implemented on a server, aspects of the user interface 116 may be limited, or the user interface 116 may even be eliminated.

The communication interface 118 may include one or more interface mechanisms for enabling communication with other devices and/or networks. In some cases, the communication interface 118 may be any means such as a device or circuitry embodied in either hardware, or a combination of hardware and software that is configured to receive and/or transmit data from/to a network and/or any other device or module in communication with the processing circuitry 110. By way of example, the communication interface 118 may be configured to enable the apparatus 102 to communicate with another computing device via a wireless network, such as a wireless local area network (WLAN), cellular network, and/or the like. Additionally or alternatively, the communication interface 118 may be configured to enable the apparatus 102 to communicate with another computing device via a wireline network. In some example embodiments, the communication interface 118 may be configured to enable communication between the apparatus 102 and one or more further computing devices via the internet. Accordingly, the communication interface 118 may, for example, include an antenna (or multiple antennas) and supporting hardware and/or software for enabling communications with a wireless communication network (e.g., a wireless local area network, cellular network, and/or the like) and/or a communication modem or other hardware/software for supporting communication via cable, digital subscriber line (DSL), universal serial bus (USB), Ethernet or other methods.

Having now described an apparatus configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

Figure 2:
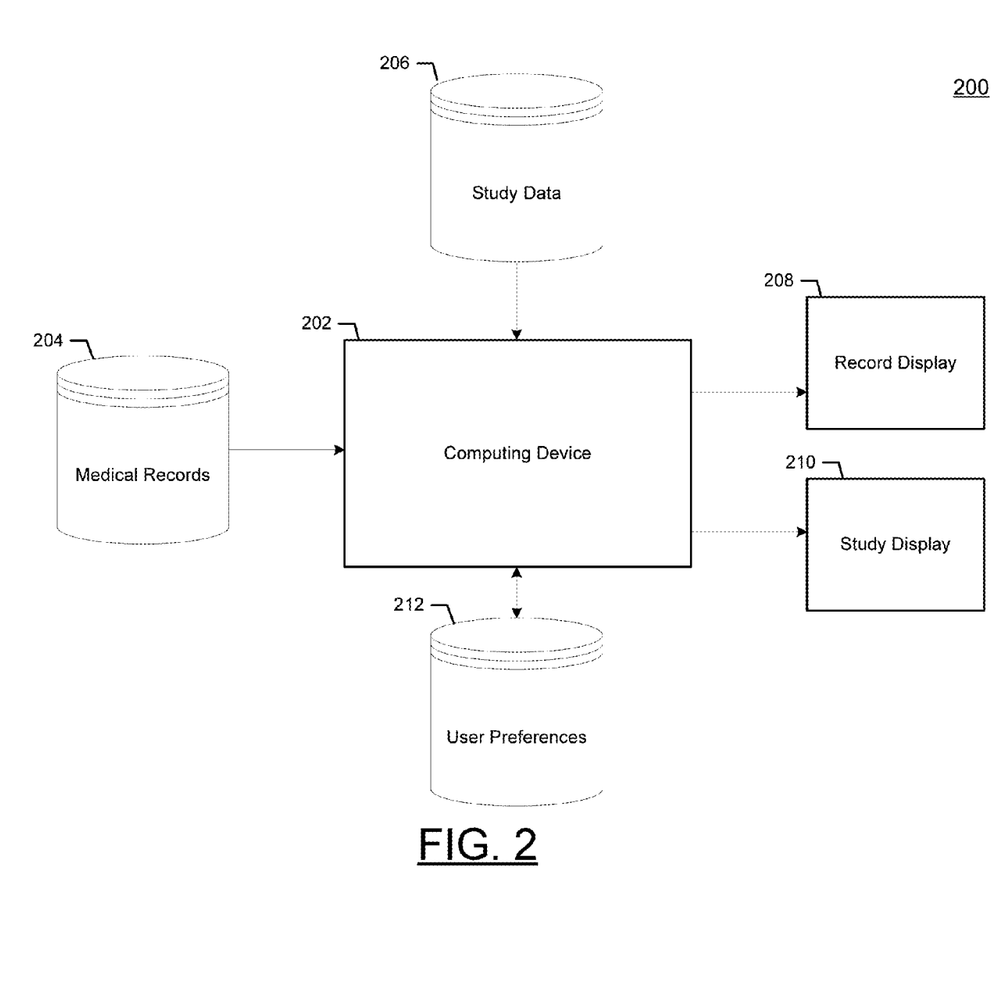
FIG. 2 is a block diagram depicting data flow among a medical imaging application, a set of medical records, an image source, a set of user preferences, and a plurality of displays in accordance with example embodiments of the present invention.

FIG. 2 is a block diagram depicting data flow 300 among a computing device 202, a set of medical records 204, study data 206, a set of user preferences 212, and a plurality of displays 208, 210 in accordance with example embodiments of the present invention. The computing device 202 may be configured as an apparatus 102 with a processor and memory as described above with respect to FIG. 1. The computing device 202 may access a medical study stored in the study data 206. The study data 206 may be stored as a file or set of files, or received directly from another device performing the study (e.g., a magnetic resonance imaging (MRI) device or a computed tomography scanner (CT)). In some embodiments, the study data 206 may be stored on a separate computing device or in a separate database external to the computing device 202. The study data 206 may include one or more images or other medical study results. In some embodiments, the study data 206 may include study metadata, such as the type of study, the time or date of the study, whether the study included a contrast medium, a viewing angle of images in the study, a patient name or other identifying information, or the like. The study data 206 may be provided in a Digital Imaging and Communications in Medicine (DICOM) format.

The computing device 202 may access the set of medical records 204 to retrieve clinical data for the patient associated with the study data 206. The medical records 204 may include patient medical data, such as lab reports, emergency room reports, electrocardiographs, medications, surgery reports, pathology reports, allergies, discharge notes, patient charts, or the like. The set of medical records 204 may be provided in a particular format, such as the Health Level 7 (HL7) format. The format may include a particular organization of data that provides a framework for exchanging, sharing, integrating, and retrieving information from health records. This format may organize the data in a way that is retrievable and accessible by the computing device 202.

The computing device 202 may process the data for the patient retrieved from the set of medical records 204 to identify clinical data that is relevant to the particular study received from the study data 206. As described above, the clinical data may be identified as being relevant to the particular procedure type of the study, the modality of the study, the patient's orientation during the study, the region of the patient's body examined in the study, or the personal preferences of the practitioner examining the study. For example, the computing device 202 may organize the clinical data such that a practitioner can access particular sets of data or individual reports that are relevant in some way to the study being viewed. As a specific example, the computing device 202 may be a Picture Archiving and Communication System (PACS) for viewing of medical images.

The computing device 202 may monitor which sets of clinical data are retrieved by users during analysis of the study to learn the sets of clinical data that are most frequently associated with the study type. Particular types of clinical data may be associated with particular studies at a user level (e.g., this particular user tends to access this set of data for this type of study), at a study level (e.g., users in general tend to access this set of data for this type of study), or in general (e.g., users tend to access this set of data for any study). The next time that a study of the same or similar type is accessed, the system may present the user with the option to select the clinical data sets previously selected for other studies of the same type. An example of an interface for selecting a set of clinical data is described further below with respect to FIGS. 3 and 4.

The computing device 202 may be coupled to a record display 208 and a study display 210. The record display 208 may display interface options for selecting sets of clinical data that are relevant to the study being displayed on the study display 210. As described above, the computing device 202 may determine sets of clinical data that are relevant to the study being displayed on the study display 210, and provide appropriate interface options. The record display may include one or more user input devices, such as a touch screen interface or a mouse or keyboard. An example of the record display 208 is described further below with respect to FIG. 4.

The study display 210 may display data relevant to a medical study being analyzed by a medical practitioner. For example, the study display 210 may be a medical imaging display, such as a display of an x-ray, an MRI, a CT scan, an electrocardiogram, an echocardiogram, an ultrasound, or any other type of medical study.

The record display 208 and the study display 210 may include any kind of display operable to display records and medical studies, respectively. Although the record display 208 and the study display 210 are described as two separate displays, embodiments may include a single display operative to display both sets of data simultaneously, or by switching between the sets of data.

Figure 3:
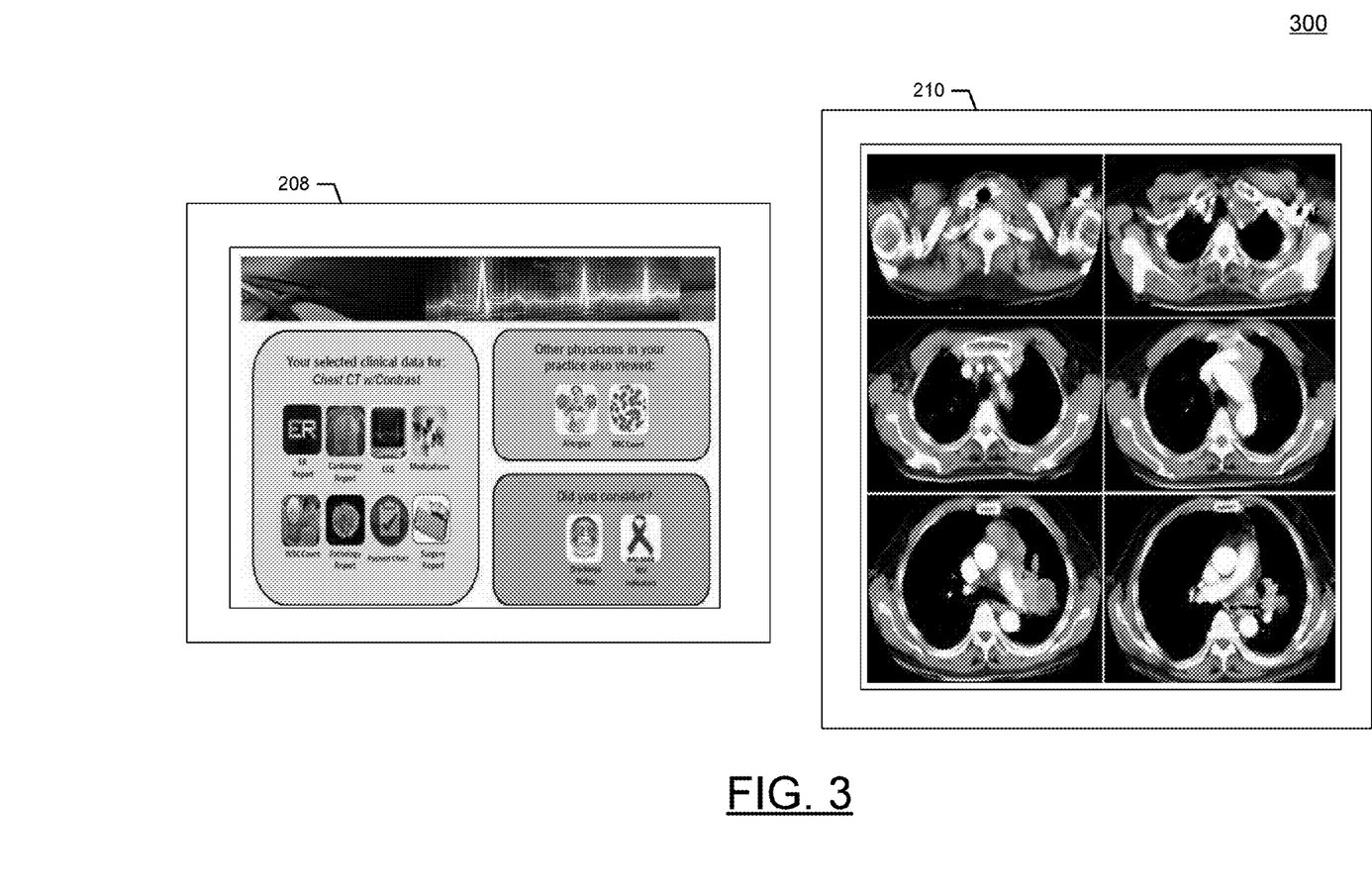
FIG. 3 is an illustration depicting an example of a plurality of displays for providing an integrated display of clinical data in accordance with example embodiments of the present invention.

FIG. 3 is an illustration depicting an example of a plurality of displays for providing an integrated display of clinical data in accordance with example embodiments of the present invention. As described with respect to FIG. 2, embodiments of the invention may include a record display 208 and a study display 210. In the instant example, the record display 208 includes a set of interface options for selecting clinical data associated with the patient associated with the CT scan displayed on the study display 210. The medical practitioner may select interface elements on the record display 208 to view the associated medical records for the patient in order to assist with analysis of the study displayed on the study display 210.

In this manner, the practitioner analyzing the study is provided with a display that integrates clinical data for the patient with a display of study data. The record display 208 may thus function as a "cockpit" or "heads up display" providing easy, efficient access to patient medical records. By integrating the record display 208 with the study display 210, the practitioner may be able to review relevant patient clinical data without switching to another device.

Figure 4:
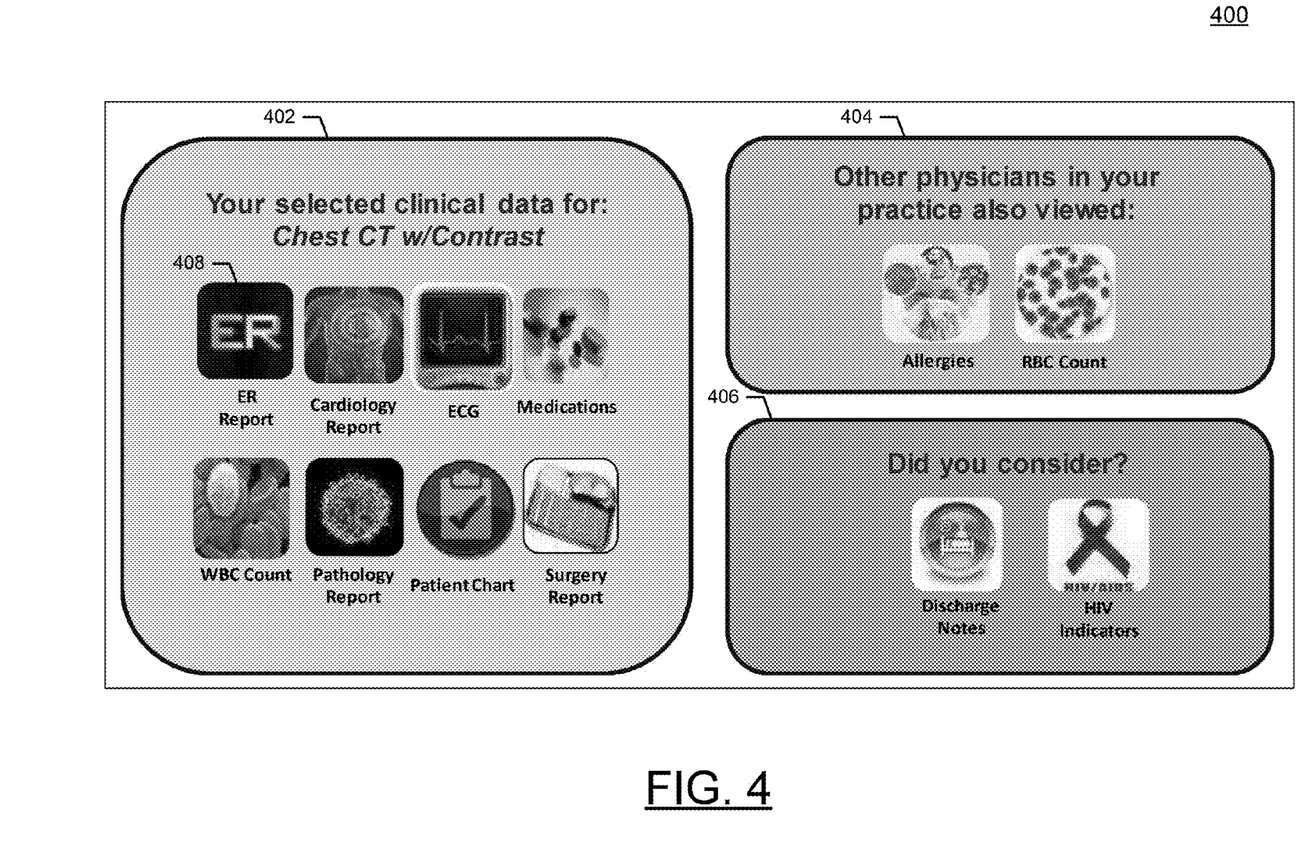
FIG. 4 is an illustration depicting an example of a clinical data display in accordance with example embodiments of the present invention.

FIG. 4 is an illustration depicting an example of a clinical data display 400 in accordance with example embodiments of the present invention. The clinical data display 400 may represent an example of an interface displayed on a record display, such as the record display 208 described with respect to FIGS. 2 and 3. In the present example, the clinical data display 400 includes a set of user icons 402, a set of icons from other users 404, and a set of additional study icons 406. The user icons 402 may include one or more individual icons 408. Each individual icon may be associated with a portion of clinical data contained within or derived from user medical records. For example, upon selection of the icon 408, the user may be presented with a copy of the patient's emergency room report. These icons 408 may be selected for inclusion in the interface 400 by virtue of their relevance to the study being examined. As described above, relevance may be determined by identifying correlations between the types of clinical data and attributes of the study being analyzed and/or the user performing the study, such as the type or modality of the study, the identity of the user, the orientation of the patient, the part of the body being examined, and the like. In some embodiments, the icon 408 may also relate to information extracted from or otherwise derived from the patient medical records. For example, the icon may launch an "app" or "widget" that provides a specific set of data, such as the patient's HIV status or whether the patient is a smoker.

The set of icons from other users 404 may be derived from learning models that monitor input from other users for the same type of studies or similar studies. For example, the interface may suggest interface options for clinical data reviewed by other practitioners for the same type of study (e.g., other radiologists). The set of additional study icons 406 may also provide interface options that are otherwise associated with the type of study being reviewed by the practitioner. For example, the set of additional study icons 406 may suggest clinical data that has not been correlated to that study type by the user, but which could be relevant based on similar preferences for procedures or study types. As a specific example, for an abdominal CT with contrast the set of additional study icons 406 may provide interface elements that allow for viewing of the patient's "Prior Surgical History" even if that data element has not been configured as a relevant data point, given that "Prior Surgical History" was defined by the user as a preference when viewing abdominal ultrasound exams. This may be based on rule that defines that both CT and ultrasound procedures may be used to diagnose perforations in abdominal organs, and therefore they could be potential correlation between any abdominal procedures and the prior surgical history of the patient.

The interface 400 may be configurable by the user. For example the user may indicate that they wish for particular sets of clinical data, applications, widgets, or other types of data to be displayed for a particular type of study. Additionally or alternatively, the interface 400 may be associated with a learning model that learns the preferences of the particular user based on past studies, and the interface may be populated with the icons, applications, and widgets identified by the learning model. For example, after a particular user has added the "HIV Status" widget to their interface three times during a thoracic CT scan study, the system may automatically add the HIV Status widget to the interface for the particular user. As another example, three other practitioners may be working within a particular radiology group. Each of these practitioners may have selected to allow the system to select widgets or sets of clinical data based on their particular sub-specialty. Based on the preferences of the first radiologist, the system may suggest adding the HIV Status widget to the other three practitioners in the group.

The user may interact with the interface in a variety of ways. For example, the user may resize the interface elements, drag and drop the interface elements to place in different parts of the screen, hover over an interface element to see additional data, or the like. In some embodiments, the display of the interface elements may be modified based on the clinical data available via those interface elements. For example, if a particular set of clinical data appears to be anomalous, the icon associated with the anomalous clinical data may be highlighted, enlarged, or otherwise altered in display to be noticeable to the user.

Figure 5:
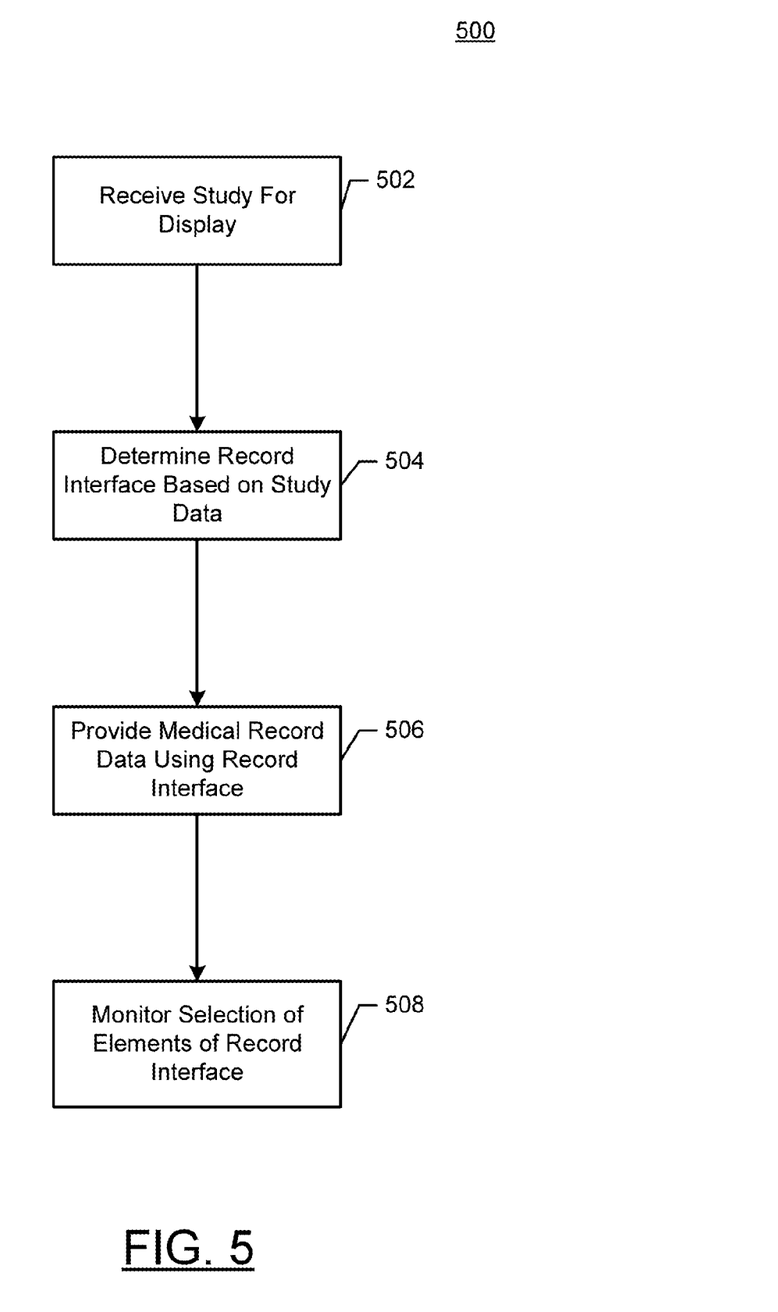
FIG. 5 is a flow diagram depicting an example of a method for providing an integrated display of clinical data in accordance with example embodiments of the present invention.

FIG. 5 is a flow diagram depicting an example of a method 500 for providing an integrated display of clinical data in accordance with example embodiments of the present invention. The method 500 describes a process by which a user may be provided with access to clinical data that is related to a medical study being viewed by the user. In this manner, the user is given straightforward, efficient access to relevant patient medical records to assist with analysis of the study.

At action 502, a study is received for display. As described above, the study may be any sort of medical study for analysis by a medical practitioner, such as a medical image. The study may include one or more files, along with a set of study metadata, such as information about the patient associated with the study, information about the type of study, information about one or more images contained within the study, or the like. The study may be received directly from an imaging device, or reviewed as a set of stored or recorded study data contained on a storage device.

At action 504, a record interface, such as the interface 400 described with respect to FIG. 4, is determined based on metadata associated with the study. As described above, one or more icons or applications may be determined for display on the interface as relevant to the selected study. For example, the interface may provide access to patient clinical data, such that selection of a particular interface option retrieves and/or displays the associated clinical data from the patient's records. In some embodiments, interface elements selected for the record interface are determined based on previously selected interface elements for the particular type of study. A method for determining interface elements based on past selected interface elements is described further below with respect to FIG. 6.

At action 506, access to patient medical records is provided using the record interface determined at action 504. Once the interface elements are identified for selection of patient medical records, the user may access the associated records by selecting the particular interface element from the display. In this manner, the user may easily select relevant clinical data for review when conducting an analysis of a medical study.

At action 508, the selection of interface elements is monitored and stored to learn the preferences of the user. In this manner, the interface may be updated to provide access to frequently viewed clinical data for future studies. An example method for learning such user preferences and providing an interface accordingly is described further below with respect to FIG. 6.

Figure 6:
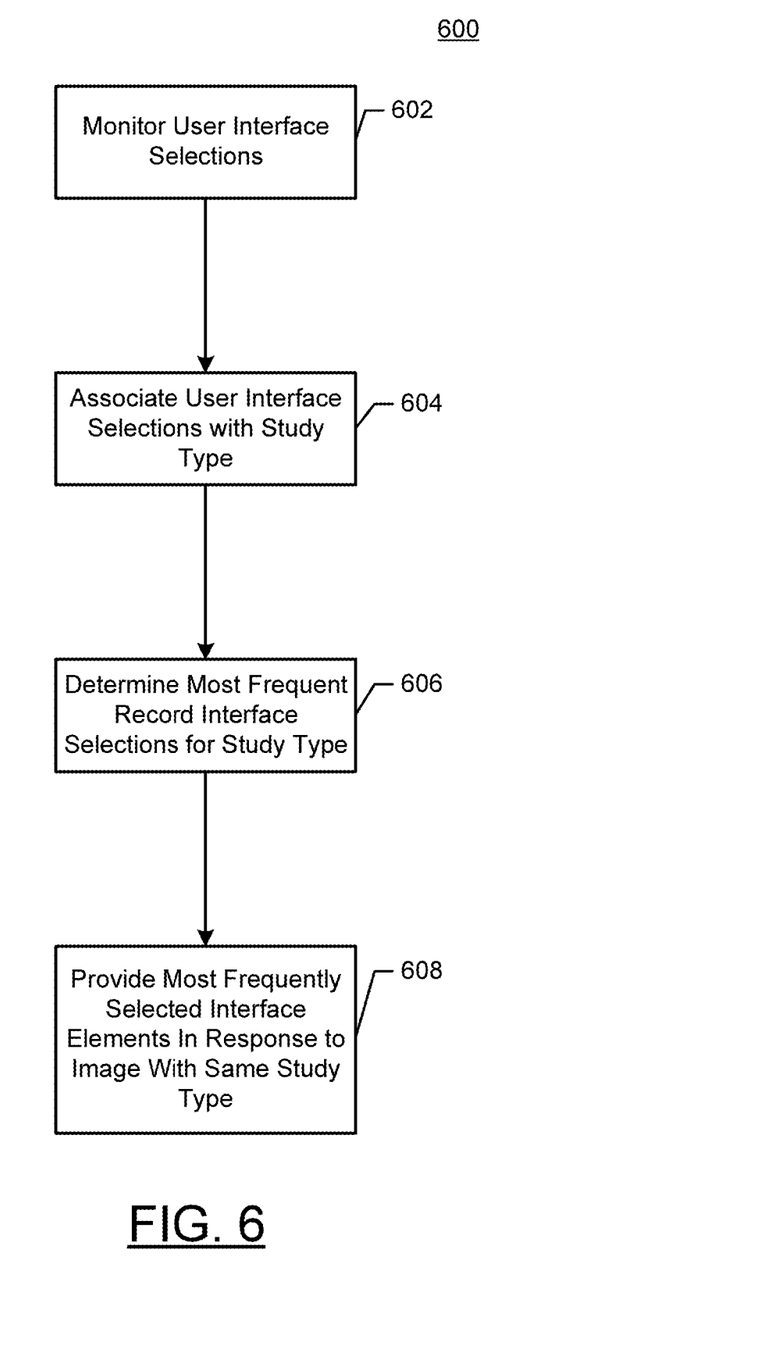
FIG. 6 is a flow diagram depicting an example of a method for providing an adaptive integrated display of clinical data in accordance with example embodiments of the present invention.

FIG. 6 is a flow diagram depicting an example of a method 600 for providing an adaptive integrated display of clinical data in accordance with example embodiments of the present invention. The method 600 provides a system with the ability to learn user preferences and adapt to those preferences. In this regard, the method 600 may track user input to determine which sets of clinical data are relevant for the user to particular types of medical studies. The user input is then associated with those medical studies, such that when the same or a similar type of study is viewed in the future, the user is presented with the opportunity to select clinical data that the user has previously identified as relevant.

At action 602, user interface selections may be monitored. For example, the particular icons, widgets, applications, or the like selected by a user (e.g., a medical practitioner) during analysis of a medical study may be monitored and stored as the user selects each interface element.

At action 604, the user interface selections may be associated with the particular type of study being analyzed by the user. For example, if the user selects an HIV Status widget when analyzing a thoracic CT scan, then the selection of the HIV status widget may be associated with the thoracic CT scan study type. The selected interface element may also be associated with the particular user, a particular category of studies (e.g., all CT scan studies), a user specialty (e.g., all radiologists, or all radiologists with a particular specialty).

At action 606, analytics are derived for the particular study and the selected interface options based on the user interface selections monitored at action 602 and associated with the study at action 604. As described above, the analytics may be stored relative to the study type, the particular user, the particular sub-specialty, or the like. These analytics may be used to learn the most relevant sets of clinical data for particular study types, for particular types of user, or the like.

At action 608, the analytics may be used to provide interface elements that are identified as relevant in response to future studies. As described at action 606, the relevancy of interface elements may be determined by the study type, by the particular user, by the type of user, and the like. In this manner, users may be provided with a concise interface to relevant clinical data to assist with analysis of medical studies. The learning model employed by the system allows for automatic configuration of the interface, without requiring the user to manually specify particular sets of clinical data for particular studies, although embodiments may also allow for such configuration.

It will be understood that each block of the flowchart, and combinations of blocks in the flowchart, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory 114 of an apparatus employing an embodiment of the present invention and executed by a processor 112 of the apparatus. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, blocks of the flowchart support combinations of means for performing the specified functions and combinations of operations for performing the specified functions for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included. Modifications, additions, or amplifications to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method comprising:
   receiving medical study data for a first medical study associated with a patient, wherein the medical study data comprises at least one medical study type defining a type of medical imaging procedure used to capture the medical study data;
   receiving an indication of a user specialty of a user;
   determining, using a processor, one or more sets of clinical data based on the medical study type and a set of study analytics associated with the at least one medical study type and the user specialty, the one or more sets of clinical data associated with electronic health records for the patient, wherein the study analytics comprise at least one analytic value reflecting a frequency with which an interface element associated with the one or more sets of clinical data is selected by users of the same user specialty for at least one different medical study of the same medical study type as the first medical study as defined by the medical study data; and
   generating an interface comprising a plurality of interface elements, the interface providing access to the one or more sets of clinical data via selection of at least one of the plurality of interface elements, wherein the interface elements are arranged based, at least in part, on the frequency with which the respective interface elements are selected according to the medical study type.

2. The method of claim 1, further comprising:
   displaying the medical study data; and
   displaying the interface.

3. The method of claim 1, wherein the one or more sets of clinical data are derived from electronic medical records.

4. The method of claim 1, wherein the medical study data comprises at least one image.

5. The method of claim 4, wherein the at least one image is stored in a Digital Imaging and Communications in Medicine format.

6. The method of claim 1, further comprising:
   monitoring an indication of a user selection of at least one of the plurality of interface elements; and
   adding the indication of the user selection to the set of study analytics.

7. The method of claim 6, wherein the set of study analytics are further associated with at least one of a particular user, or a particular class of users.

8. The method of claim 1, wherein the one or more sets of clinical data comprise at least one of an emergency room report, a cardiology report, an electrocardiogram, a list of patient medications, a lab report, a pathology report, a patient chart, or a list of patient allergies.

9. The method of claim 1, wherein the interface comprising a plurality of interface elements includes a first arrangement of interface elements associated with a first medical study type in response to the first medical study being of the first medical study type, and a second, different arrangement of interface elements associated with a second medical study type in response to the first medical study being of the second medical study type.

10. The method of claim 1, wherein the user specialty comprises a medical discipline specialty.

11. An apparatus comprising processing circuitry configured to:
    receive medical study data for a first medical study associated with a patient, wherein the medical study data comprises at least one medical study type defining a type of medical imaging procedure used to capture the medical study data;
    receive an indication of a specialty of a user;
    determine one or more sets of clinical data based on the medical study type and a set of study analytics associated with the at least one medical study type and the user specialty, the one or more sets of clinical data associated with electronic health records for the patient, wherein the study analytics comprise at least one analytic value reflecting a frequency with which an interface element associated with the one or more sets of clinical data is selected by users of the same user specialty for at least one different medical study of the same medical study type as the first medical study as defined by the medical study data; and generate an interface comprising a plurality of interface elements, the interface providing access to the one or more sets of clinical data via selection of at least one of the plurality of interface elements, wherein the interface elements are arranged based, at least in part, on the frequency with which the respective interface elements are selected according to the medical study type.

12. The apparatus of claim 11, further configured to:
display the medical study data; and
display the interface.

13. The apparatus of claim 11, wherein the one or more sets of clinical data are derived from electronic medical records.

14. The apparatus of claim 11, wherein the medical study data comprises at least one image.

15. The apparatus of claim 14, wherein the at least one image is stored in a Digital Imaging and Communications in Medicine format.

16. The apparatus of claim 11, further configured to:
monitor an indication of a user selection of at least one of the plurality of interface elements; and
adding the indication of the user selection to the set of study analytics.

17. The apparatus of claim 16, wherein the set of study analytics are further associated with at least one of, a particular user, or a particular class of users.

18. The apparatus of claim 11, wherein the one or more sets of clinical data comprise at least one of an emergency room report, a cardiology report, an electrocardiogram, a list of patient medications, a lab report, a pathology report, a patient chart, or a list of patient allergies.

* * * * *